US007439399B2

United States Patent
Aronhime et al.

(10) Patent No.: US 7,439,399 B2
(45) Date of Patent: Oct. 21, 2008

(54) PROCESSES FOR THE PREPARATION OF ATOMOXETINE HYDROCHLORIDE

(75) Inventors: Judith Aronhime, Rehovot (IL); Stefano Bianchi, Como (IT); Eugenio Castelli, Arlate di Calco (IT); Paola Daverio, Villasanta (IT); Silvia Mantovani, Cesano Maderno (IT); Adrienne Kovacsne-Mezei, Debrecen (HU)

(73) Assignee: Teva Pharmaceutical Fine Chemicals, Bulciago (IT)

( * ) Notice: Subject to any disclaimer, the term of this patent is extended or adjusted under 35 U.S.C. 154(b) by 215 days.

(21) Appl. No.: 11/219,785

(22) Filed: Sep. 7, 2005

(65) Prior Publication Data

US 2006/0211772 A1 Sep. 21, 2006

Related U.S. Application Data

(63) Continuation-in-part of application No. 11/169,995, filed on Jun. 28, 2005.

(60) Provisional application No. 60/583,641, filed on Jun. 28, 2004, provisional application No. 60/609,716, filed on Sep. 14, 2004, provisional application No. 60/622,065, filed on Oct. 25, 2004, provisional application No. 60/652,330, filed on Feb. 11, 2005, provisional application No. 60/583,644, filed on Jun. 28, 2004, provisional application No. 60/652,332, filed on Feb. 11, 2005, provisional application No. 60/583,643, filed on Jun. 28, 2004, provisional application No. 60/652,331, filed on Feb. 11, 2005, provisional application No. 60/666,666, filed on Mar. 30, 2005, provisional application No. 60/675,369, filed on Apr. 26, 2005, provisional application No. 60/689,778, filed on Jun. 9, 2005, provisional application No. 60/690,738, filed on Jun. 14, 2005.

(51) Int. Cl.
*C07C 213/08* (2006.01)

(52) U.S. Cl. ...................................... 564/347; 564/348

(58) Field of Classification Search ....................... None
See application file for complete search history.

(56) References Cited

U.S. PATENT DOCUMENTS

| 4,018,895 | A | | 4/1977 | Molloy et al. |
| 4,194,009 | A | * | 3/1980 | Molloy et al. ............... 514/651 |
| 4,777,291 | A | | 10/1988 | Misner |
| 4,868,344 | A | | 9/1989 | Brown |
| 4,970,232 | A | * | 11/1990 | Jakobsen et al. ............. 514/466 |
| 5,019,592 | A | * | 5/1991 | Jakobsen et al. ............. 514/524 |
| 5,658,590 | A | | 8/1997 | Heiligenstein et al. |
| 6,333,198 | B1 | | 12/2001 | Edmeades et al. |
| 6,541,668 | B1 | | 4/2003 | Kjell et al. |

FOREIGN PATENT DOCUMENTS

| DE | 41 23 253 A1 | 1/1993 |
| EP | 0 052 492 A1 | 5/1982 |
| EP | 0 193 405 A1 | 9/1986 |
| EP | 0 721 777 A2 | 1/1995 |
| WO | WO 94/00416 | 1/1994 |
| WO | WO 00/58262 | 10/2000 |
| WO | WO 00/64855 | 11/2000 |
| WO | WO 2006/004923 A2 | 1/2006 |
| WO | WO 2006/004976 | 1/2006 |
| WO | WO 2006/004977 A2 | 1/2006 |
| WO | WO 2006/004979 A2 | 1/2006 |
| WO | WO 2006/020348 A2 | 2/2006 |
| WO | WO 2006/068662 A1 | 6/2006 |

OTHER PUBLICATIONS

Srebnik, M. et al. "Chiral Synthesis via Organoboranes. 18. Selective Reductions. 43. Dissopinocampheylchloroborane as an Excellent . . . " J. Org. Chem. (1988), vol. 53, p. 2916-2920.
Anon (R)-(−)-N-Methyl-3-(2-Methylphenoxy)Phenyl-3-Phenylpropylamine (S)-(+)-Mandelate Chemical Abstracts Service XP-002367856 Dec. 29, 2004.
Koenig, T.M. et al. "A Convenient Method for Preparing Enantiomerically Pure Norfluoxetine, Fluoxetine and Tomoxetine" Tetrahedron Letters, vol. 35, No. 0, pp. 1339-1342 (1994).
Strobel, H.A.; Heineman, W.R., Chemical Instrumentation: A Systematic Approach, 3rd dd. (Wiley & Sons: New York 1989)—pp. 391-393, 879-894, 922-925, 953.
Snyder, L.R.; Kirkland, J.J., Introduction to Modern Liquid Chromatography, 2nd ed. (John Wiley & Sons: New York 1979)—p. 549-552, 571-572.
Sellers, J.A. et al. "Determination of the Enantiomer and Positional Isomer Impurities in Atomoxetine Hydrochloride with Liquid Chromatography Using Polysaccharide Chiral Stationary Phases." J. of Pharmaceutical and Biomedical Analysis, vol. 41, pp. 1088-1094 (2006).

* cited by examiner

*Primary Examiner*—Brian J Davis
(74) *Attorney, Agent, or Firm*—Kenyon & Kenyon LLP

(57) ABSTRACT

The present invention provides improved processes for the preparation of atomoxetine hydrochloride under reaction conditions that improve reaction yields and facilitate commercial synthesis. In particular, the invention is directed to the synthesis of atomoxetine HCl by adding HCl to a mixture of (R)-(−)-tomoxetine (S)-(+)-mandelate with an organic solvent, with or without a base and water. In preferred embodiments, the atomoxetine hydrochloride produced is Form A.

23 Claims, 1 Drawing Sheet

PROCESSES FOR THE PREPARATION OF ATOMOXETINE HYDROCHLORIDE

CROSS-REFERENCE TO RELATED APPLICATIONS

This application is a continuation-in-part of U.S. patent application Ser. No. 11/169,995, filed Jun. 28, 2005, as well as the benefit of U.S. Provisional Patent Application Nos. 60/583,641, filed Jun. 28, 2004, 60/609,716, filed Sep. 14, 2004, 60/622,065, filed Oct. 25, 2004, 60/652,330, filed Feb. 11, 2005, 60/583,644, filed Jun. 28, 2004, 60/652,332, filed Feb. 11, 2005, 60/583,643, filed Jun. 28, 2004, 60/652,331, filed Feb. 11, 2005, 60/666,666, filed Mar. 30, 2005, 60/675, 369, filed Apr. 26, 2005, Application No. 60/689,778, filed Jun. 9, 2005, and Application No. 60/690,738, filed Jun. 14, 2005, the contents of all of which are incorporated herein by reference.

FIELD OF THE INVENTION

The present invention relates to processes for preparing atomoxetine hydrochloride. The atomoxetine hydrochloride can be in a crystalline form referred to herein as Form A.

BACKGROUND OF THE INVENTION

Atomoxetine HCl is a selective norepinephrine reuptake inhibitor. It is marketed under the name STRATTERA® for the treatment of Attention-Deficit/Hyperactivity Disorder (ADHD) and is available in 10 mg, 18 mg, 25 mg, 40 mg, and 60 mg dosage forms.

Atomoxetine, chemically known as (R)-(−)-N-methyl-3-(2-methylphenoxy)-3-phenylpropylamine, has the following structure:

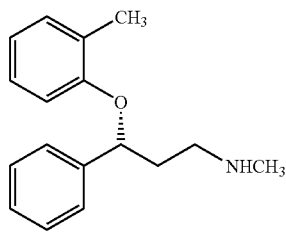

Atomoxetine, the (R)-(−) enantiomer of tomoxetine, is an aryloxyphenylpropylamine. It is about twice as effective as the racemic mixture and about nine times more effective than the (+)-enantiomer, as disclosed in U.S. Pat. No. 4,018,895 (assigned to Eli Lilly and Co.), EP 0 052 492 (Eli Lilly and Co.), and EP 0 721 777 (Eli Lilly and Co.).

Several processes for synthesizing 3-aryloxy-3-phenylpropylamines are known in the art. For example, U.S. Pat. No. 4,018,895 assigned to Eli Lilly and Co. discloses an aliphatic nucleophilic displacement of N-protected-3-halogen-3-phenylpropylamines by phenols, followed by N-deprotection. U.S. Pat. No. 4,868,344 assigned to Aldrich-Boranes, Inc. relates to the Mitsunobu reaction between 3-hydroxy-3-phenylpropylhalides and phenols, followed by amination of the resulting 3-aryloxy-3-phenylpropylhalides. Tomoxetine is also synthesized by the processes disclosed in U.S. Pat. No. 6,541,668 and WO 00/58262 (assigned to Eli Lilly and Co.) and WO 94/00416 (by Richter Gedeon Vegyeszeti Gyar RT). These documents disclose an aromatic nucleophilic displacement of an aryl halide by 3-hydroxy-3-phenylpropylamines under strongly basic conditions. The nucleophilic aromatic displacement process disclosed in WO 00/58262 includes reacting N-methyl-3-hydroxy-3-phenylpropylamine with a protected 2-fluorobenzaldehyde to produce tomoxetine after several functional group interconversion steps.

EP Patent No. 0 052 492 discloses a process for the preparation of atomoxetine HCl. In this process, (R)-(−)-tomoxetine (S)-(+)-mandelate is first basified in water to eliminate the mandelate, then extracted in diethyl ether. HCl gas is bubbled into the solution to obtain (R)-(−)-tomoxetine (atomoxetine) hydrochloride. Yields are reported as approximately 77%-90%.

Similarly, U.S. Pat. No. 6,541,668, assigned to Eli Lilly and Co., discloses a process for the preparation of atomoxetine HCl involving basifying the mandelate salt, followed by extracting with t-butyl methyl ether, removing water by azeotropic distillation, and adding hydrogen chloride. This process is inefficient due to long process time, low product yields, and the use of hazardous solvents that are incompatible with large-scale industrial synthesis.

Thus, there is a need in the art for processes for the preparation of atomoxetine hydrochloride that will produce higher yields and that will facilitate commercial production.

Repetition of the processes disclosed in EP Patent No. 0 052 492 and U.S. Pat. No. 6,541,668 yielded a crystalline form of atomoxetine HCl, denominated Form A. Form A can be characterized by a powder x-ray diffraction pattern having peaks at about 13.7, 17.3, 18.7, 21.1, 22.6, 24.0, 27.3, 28.4 and 29.3±0.2 degrees two-theta, and further characterized by a powder x-ray diffraction pattern having peaks at about 8.5, 13.3, 13.7, 14.7, 17.9, 22.3, 25.0, 25.4, 25.7, 26.4, 29.8 and 32.0±0.2 degrees two-theta, substantially as depicted in FIG. 1.

Those skilled in the pharmaceutical arts understand that crystallization of an active pharmaceutical ingredient offers the best method for controlling important qualities like chemical quality, particle size, and polymorphic content. Thus, there is a need for crystal forms of atomoxetine hydrochloride and processes to produce such forms. The forms should be suitable for pharmaceutical use.

SUMMARY OF THE INVENTION

The present invention provides improved processes for the preparation of atomoxetine hydrochloride under reaction conditions that improve reaction yields and facilitate commercial synthesis. In particular, the invention is directed to the synthesis of atomoxetine HCl comprising:

a) combining a mixture of (R)-(−)-tomoxetine (S)-(+)-mandelate with an organic solvent to obtain a reaction mixture;
  b) combining the reaction mixture with HCl to obtain atomoxetine HCl; and
  c) recovering atomoxetine HCl.

In another aspect, the present invention provides a process for preparing atomoxetine HCl comprising:

a) combining a mixture of (R)-(−)-tomoxetine (S)-(+)-mandelate and an organic solvent in the presence of water and a base to obtain atomoxetine free base;
  b) combining the atomoxetine free base with HCl to obtain atomoxetine HCl; and
  c) recovering the atomoxetine HCl.

Preferably, the amount of water is about 3 to about 7 ml per 1 gram of the starting material. Most preferably, the amount of water is about 5 ml per 1 gram of the starting material.

In yet another aspect, the present invention provides a process for preparing atomoxetine HCl comprising combining N-methyl-3-hydroxy-3-phenylpropylamine with 2-fluorotoluene in the presence of about 0.1 to about 20 moles DMSO and an alkali metal hydroxide to obtain a tomoxetine racemate, separating the desired (R)-(−)-tomoxetine from the (S)-(+)-tomoxetine in a (S)-(+)-mandelate form; and reacting the mandelate with HCl to obtain atomoxetine HCl.

In yet another aspect, the atomoxetine HCl obtained by these processes is crystalline atomoxetine hydrochloride Form A.

DETAILED DESCRIPTION OF THE INVENTION

Figure 1:
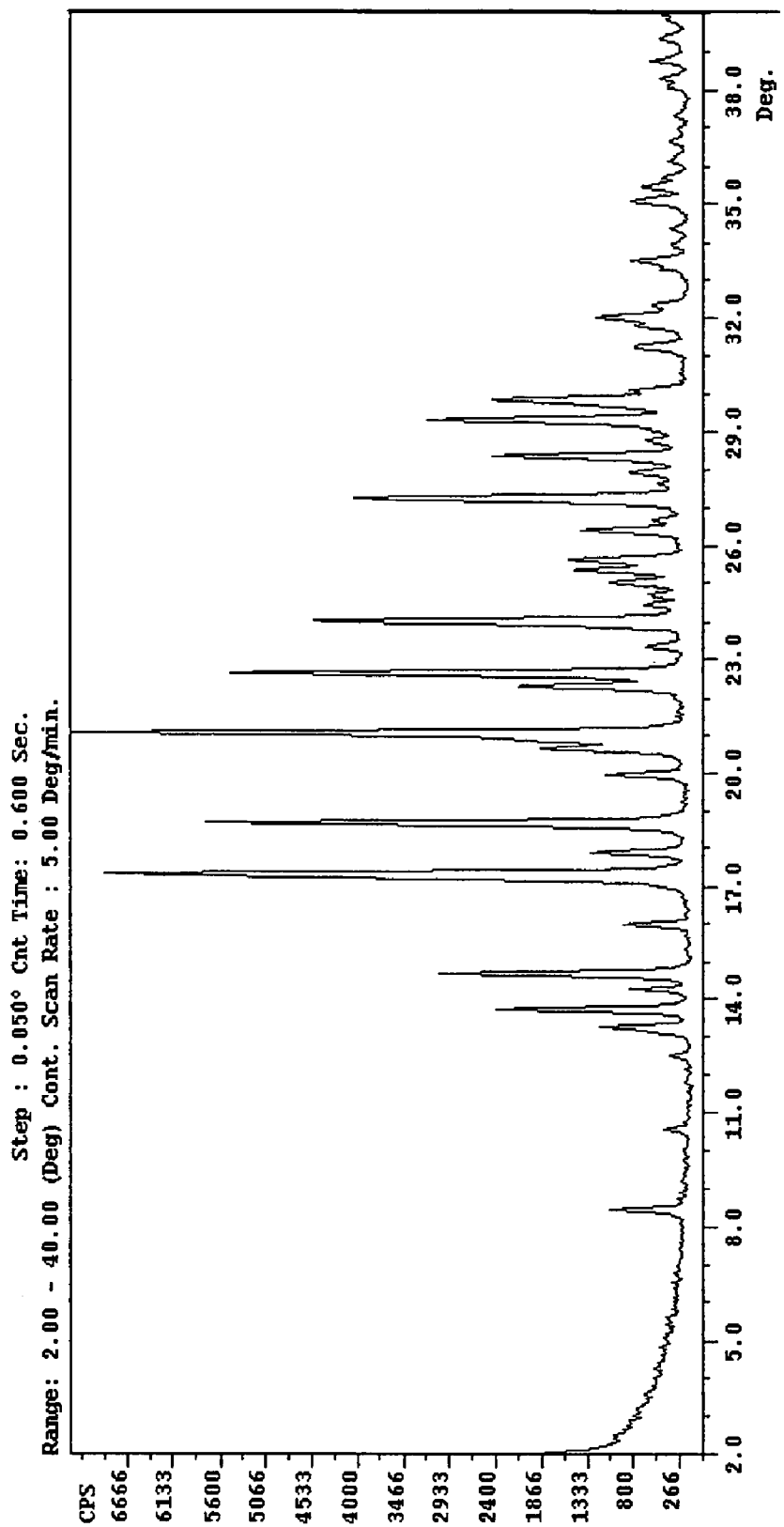
FIG. 1 is a characteristic powder x-ray diffraction spectrum of atomoxetine hydrochloride Form A.

As used herein the term "aromatic solvent" refers to a $C_{6-10}$ aromatic hydrocarbon such as but not limited to benzene, xylene, or toluene.

As used herein, "room temperature" is meant to indicate a temperature of about 18-25° C., preferably about 20-22° C.

The present invention provides improved processes for the preparation of atomoxetine under reaction conditions that improve reaction yields and facilitate the process. In particular, the present invention is directed to the synthesis of atomoxetine hydrochloride by combining a mixture of (R)-(−)-tomoxetine (S)-(+)-mandelate and an organic solvent with HCl.

By producing atomoxetine HCl by direct displacement of (S)-(+)-mandelic acid by hydrochloric acid, it is believed that the processes of the present invention are more efficient than those disclosed in prior art. It is further believed that the processes of the present invention produce atomoxetine HCl in high yields, for example about 85 to about 95%. Furthermore, for embodiments that use (R)-(−)-tomoxetine (S)-(+)-mandelate in an enantiomeric ratio higher than 99:1, the enantiomeric excess of the atomoxetine HCl obtained is expected to be higher than 98%. The processes of the present invention preferably avoid the use of solvents that may be harmful to the environment, such as ethers and dichloromethane, which are required in some prior art processes for the preparation of atomoxetine HCl, such as the processes disclosed in EP Patent No. 0 052 492.

In one embodiment, a process is provided for the synthesis of atomoxetine HCl comprising combining (R)-(−)-tomoxetine (S)-(+)-mandelate and an organic solvent to obtain a reaction mixture, followed by combining the reaction mixture with HCl, either as a gas or an aqueous solution, to obtain a slurry. Preferably, the temperature is maintained at about 15° C. to about 50° C. when HCl is added. The slurry is maintained, preferably by stirring, for a sufficient time to obtain atomoxetine HCl, which is then recovered.

Another embodiment of the present invention provides a process for preparing atomoxetine hydrochloride, comprising providing a mixture containing (R)-(−)-tomoxetine (S)-(+)-mandelate, an organic solvent and water, and combining the mixture with a base to obtain a biphasic mixture containing atomoxetine free base. Preferably, the amount of water is about 3 to about 7 ml per 1 gram of the starting material. Most preferably, the amount of water is about 5 ml per 1 gram of the starting material. Preferably, the base is selected from the group consisting of NaOH, KOH, $Na_2CO_3$, and $K_2CO_3$. Most preferably, the base is NaOH. After the phases are separated, HCl is added, either as gas or as an aqueous solution. Preferably, prior to adding HCl, the water content of the organic phase is less than about 1%. It is also preferred that the temperature is maintained at about 15° C. to about 20° C. when HCl is added.

Preferably the organic solvent used in the processes described above for preparing atomoxetine hydrochloride is selected from the group consisting of aliphatic or aromatic hydrocarbons such as $C_{5-8}$ alkanes, toluene, and xylene; $C_{1-4}$ alkyl esters such as methyl acetate, ethyl acetate, n-butyl acetate, and iso-butyl acetate; ketones such as methyl-ethyl ketone; and linear or branched $C_{4-8}$ alcohols such as n-butanol, 2-butanol, and n-pentanol. Most preferably, the organic solvent is selected from the group consisting of ethyl acetate, n-butyl acetate, and iso-butyl acetate.

In a particular embodiment, the atomoxetine hydrochloride obtained according to the above processes is atomoxetine hydrochloride Form A.

In a particular embodiment, the present invention provides a process for the preparation of atomoxetine hydrochloride comprising the following steps:

a) combining N-methyl-3-hydroxy-3-phenylpropylamine with dimethylsulfoxide (DMSO) in the presence of an alkali metal hydroxide to form a slurry;

b) adding 2-fluorotoluene to the slurry to obtain a reaction mixture;

c) heating the resultant mixture to obtain tomoxetine;

d) combining the obtained tomoxetine with a $C_{1-4}$ alcohol, an aromatic solvent, and (S)-(+)-mandelic acid, e) heating the mixture to a temperature of about 60° C. to about 80° C.;

f) crystallizing (R)-(−)-tomoxetine (S)-(+)-mandelate from the reaction mixture;

g) adding an organic solvent, water, and a base to the salt of step f);

h) combining the mixture of step g) with HCl to form atomoxetine hydrochloride; and i) recovering the atomoxetine hydrochloride.

In a particular embodiment, the recovered atomoxetine hydrochloride is Form A.

In a preferred embodiment, the resultant mixture in step c) is heated to a temperature of about 80° C. to about 145° C. Preferably, when the amount of the alkali metal hydroxide added in step a) is about 3 mole equivalents per mole equivalent of N-methyl-3-hydroxy-3-phenylpropylamine, the resultant mixture is heated to a temperature from about 135° C. to about 145° C. Preferably, when the amount of the alkali metal hydroxide added in step a) is about 5 mole equivalents per mole equivalent of N-methyl-3-hydroxy-3-phenylpropylamine, the resultant mixture is heated to a temperature of about 80° C. to about 100° C.

Preferably, the amount of DMSO is about 0.1 to about 20 moles per moles of N-methyl-3-hydroxy-3-phenylpropylamine, and the preferred base is KOH. The mixture obtained in step a) is maintained preferably by heating the mixture to a temperature from about 80° C. to about 150° C., to obtain racemic tomoxetine.

Alternatively, step g) can be performed in the presence of an organic solvent only.

Prior to step g), the obtained (R)-(−)-tomoxetine (S)-(+)-mandelate is preferably recrystallized from a solution comprising an aromatic solvent and a $C_{1-4}$ alcohol, in order to increase the enantiomeric purity.

The reaction mixture obtained in step (f) is a biphasic system, thus the two phases are separated, and the HCl in step h) is added to the organic phase.

Atomoxetine HCl can be separated from the reaction mixture by techniques known in the art, such as filtration. The product can be washed with an organic solvent. The product can then be dried, preferably under reduced pressure.

A preferred $C_{1-4}$ alcohol is methanol. Preferably, the aromatic solvent is toluene.

To increase the yield of the above process, the (S)-(+)-tomoxetine in the solvent mixture ("mother liquor," from which (R)-(−)-tomoxetine (S)-(+)-mandelate was obtained) can be racemized by combining it with an aprotic dipolar solvent and a base having a highly ionic counter ion. Preferably, the mixture is heated. Step (d) is then repeated to further resolve the (R)-(−)-tomoxetine (S)-(+)-mandelate.

In preferred embodiments, the processes disclosed herein provide pure atomoxetine hydrochloride Form A. That is, at least about 90%, preferably at least about 95%, or more preferably at least about 99% of the atomoxetine hydrochloride produced is Form A.

Moreover, the present invention provides a process for preparing a pharmaceutical composition comprising R(−)-tomoxetine (atomoxetine) or a pharmaceutically acceptable salt thereof, which comprises bringing R(−)-tomoxetine (atomoxetine) or a pharmaceutically acceptable salt thereof prepared by a method disclosed herein into contact with one or more pharmaceutically acceptable carriers or excipients.

Having described the invention with reference to particular preferred embodiments and illustrative examples, those in the art may appreciate modifications to the invention as described and illustrated that do not depart from the spirit and scope of the invention as disclosed in the specification. The examples are set forth to aid in understanding the invention but are not intended to, and should not be construed to limit its scope in any way. The examples do not include detailed descriptions of conventional methods. Such methods are well known to those of ordinary skill in the art and are described in numerous publications. All references mentioned herein are incorporated in their entirety.

Experimental Techniques

Achiral HPLC Analysis
Instrument: HPLC Hewlett Packard VWD detector HP1100
Column: YMC ODS-AQ 250 mm×4.6 mm (i.d.) cod. AQ-303
Mobile phase: $NaH_2PO_4$ 0.02M pH 3
Buffer: acetonitrile gradient
Flow: 1.5 ml/min
Temperature: 40° C.
Wavelength: 215 nm
Chiral HPLC Analysis
Instrument: HPLC Hewlett Packard VWD detector HP1100
Column: CHIRACEL OD-R cellulose tris (3,5-dimethylphenylcarbamate)
250 mm×4.60 mm×10 mm (Daicel Chemicals cat. N° DAIC14625)
Mobile phase: KPF6 100 mM/Acetonitrile-60/40
Flow: 0.8 ml/min
Temperature: 35° C.
Wavelength: UV, 215 nm Powder x-ray diffraction data were obtained by ARL X-Ray powder diffractometer model X'TRA-030, Peltier detector, round standard aluminum sample holder with round zero background quartz plate was used. Scanning parameters: range: 2-40 deg. 2θ, continuous scan, rate: 3 deg./min. The accuracy of peak positions was defined as +/−0.2 degrees due to such experimental differences as instrumentation, sample preparations etc. Data were obtained with a Bruker D8 Discover equipped with a xyz translation stage (with x, y, z travel of 100 mm, 150 mm and 100 mm, respectively). The x-ray detector was a high-performance HI-STAR two-dimensional detector that was set to 15 cm from the centre of the goniometer. At this distance, the detector has a typical FWHM of 0.15-0.2 degrees in 2θ. The x-ray generator was typically set to 40 KV and 40 mA. The data was collected in one frame with a typical data acquisition time of 3 minutes. The 2θ range covered by the HI-STAR detector is from 4.5 to 39.5 degrees. The sample is typically oscillated in the y direction (perpendicular to the x-ray travel direction) with oscillation amplitude of ±2-3 mm. Omega-scan (rocking the x-ray source and the detector synchronously) was also used occasionally to reduce preferred orientation in samples that were producing very spotty diffraction patterns. Crystals grown on a universal substrate were analyzed either uncrushed or crushed. The crushing of crystalline samples was achieved with a pneumatic compactor that has 96 pins whose diameter is 0.25 inches, sufficient to encompass the area of the samples. The force on each pin was about 12 lb. Epoch software was used to facilitate the translation of the stage to the elements of interest and a joystick to control translation and a knob to adjust the Z height were used to focus the beam on samples of interest. Epoch then stored the images and coordinates of each of the user specified locations to the database. Epoch was also used to control the data acquisition and stored the acquisition parameters, area plots, and 2-theta plots to the database as one experiment.

EXAMPLES

Example 1

(R,S)-N-methyl-3-(2-methylphenoxy)-3-phenylpropylamine (Tomoxetine Synthesis)

1100 g (14.1 mol) of dimethylsulfoxide, 200 g (1.21 mol) of N-methyl-3-hydroxy-3-phenylpropylamine and 221 g (3.63 mol) of potassium hydroxide (bulk industrial grade, 92.1% assay) were heated under stirring at 110° C. The mixture was then concentrated by vacuum distillation until about 130 g of solvent were removed. The mixture was allowed to cool to 80° C., then 400 g (3.63 mol) of 2-fluorotoluene were added. The mixture was heated to reflux (145° C.-147° C.) for one hour, and allowed to cool to about 90° C. 1000 ml of water and 1000 ml of toluene were added. The mixture was stirred for some minutes, at which time the phases were separated. The aqueous phase was extracted with 2×200 ml of toluene. The organic phases were collected and washed with 3×200 ml of water. Final organic phase weight: 1700 g. Tomoxetine content: 16.83% by weight (HPLC assay). Yield: 92.7%.

Example 2

(R)-(−)-Tomoxetine (S)-(+)-Mandelate (Tomoxetine Optical Resolution)

A solution in toluene of crude racemic tomoxetine (276.13 g, 1.081 mol, by HPLC assay) prepared as described in Example 1 was concentration in vacuum to remove water. The residue was taken up with 2025 ml of toluene and 26 ml of methanol. To the obtained solution 94 g (0.618 mol) of (S)-(+)-mandelic acid were added at 25° C. All solids were solubilized by heating to 65°-70° C. The crude mandelate salt was crystallized on cooling. The solid was isolated by filtration at 5°-10° C., washed with about 300 ml of toluene and dried in vacuo. Weight: 178 g. Tomoxetine content: 63.2% by weight (HPLC assay). Yield: 43.15%. Crude mandelate salt (R)-(−)-Tomoxetine enantiomeric ratio: R/S is about 95/5 (by chiral HPLC).

163 g of the obtained crude mandelate salt were re-crystallized from 489 ml of toluene and 49 ml of methanol as follows: the salt was solubilized by heating to 65°-70° C., then (R)-(−)-tomoxetine (S)-(+)-mandelate was crystallized on cooling, isolated by filtration at 5°-10° C., washed with about 2×90 ml of toluene and dried in vacuum. Weight: 153 g. Tomoxetine content: 63.97% by weight (HPLC assay). Yield: 38.7% from racemic tomoxetine. (R)-(−)-tomoxetine (atomoxetine) enantiomeric ratio: R/S>99/1 (by chiral HPLC).

Example 3

(R)-(−)-N-methyl-3-(2-methylphenoxy)-3-phenyl-propylamine hydrochloride (Atomoxetine Hydrochloride)

27.88 g (0.0684 mol) of (R)-(−)-tomoxetine (S)-(+)-mandelate were mixed under stirring with 138 ml of ethyl acetate and 138 ml of water. 10.89 g (about 0.08 mol) of 30% aqueous sodium hydroxide were added. The phases were then separated. The organic phase was washed with 2×47 ml of water, then it was refluxed (73°-74° C.) with a Dean-Stark condenser until water content was below 1%. Keeping the temperature between 18° C. and 20° C. by means of water-ice bath cooling, 7 g (0.07 mol) of aqueous 36% hydrogen chloride was dropped into the solution under stirring. The hydrochloride then crystallized. The obtained suspension was stirred between 18° C. and 20° C. for one hour, the solid was collected by filtration, washed with 2×10 ml of ethyl acetate and dried in vacuum. Tomoxetine hydrochloride content: >99% by HPLC assay. Weight: 16.75 (0.0575 mol) g. Yield: 84%. Atomoxetine hydrochloride enantiomeric ratio: R/S>99/1 (by chiral HPLC).

Example 4

(R)-(−)-N-methyl-3-(2-methylphenoxy)-3-phenyl-propylamine hydrochloride (Atomoxetine Hydrochloride)

45 g (0.110 mol) of (R)-(−)-tomoxetine (S)-(+)-mandelate were mixed under stirring with 225 ml of toluene and 225 ml of water. Keeping the temperature at about 40° C. by means of gentle heating, 21 g (about 0.16 mol) of 30% aqueous sodium hydroxide were added. The phases were then separated. The organic phase was washed with 100 ml of 1% aqueous sodium hydroxide, then filtered on paper and concentrated in vacuum to give 29.67 g of an oil containing 26.8 g of tomoxetine (by HPLC assay).

23.5 g of the oil were dissolved in 211 ml of ethyl acetate under stirring then, keeping temperature between 12° C. and 18° C. by means of water-ice bath cooling; gaseous hydrogen chloride was bubbled into the solution until acid reaction of litmus paper. The hydrochloride then crystallized. The obtained suspension was stirred at about 15° C. for one hour, then the solid was collected by filtration, washed with ethyl acetate and dried in vacuo. Tomoxetine hydrochloride content: >99% by HPLC assay. Weight: 24.3 g (0.0832 mol). Yield: 95%. Atomoxetine hydrochloride enantiomeric ratio: R/S>99/1 (by chiral HPLC).

Example 5

(R)-(−)-N-methyl-3-(2-methylphenoxy)-3-phenyl-propylamine hydrochloride (Atomoxetine Hydrochloride)

5.17 g (0.01267 mol) of (R)-(−)-tomoxetine (S)-(+)-mandelate were mixed at room temperature with 25.5 ml of n-butyl acetate (and 0.6 ml of toluene added to simulate use of wet (R)-(−)-tomoxetine (S)-(+)-mandelate) under stirring. Keeping the temperature between 18° C. and 20° C. by means of water-ice bath cooling, 1.4 g of aqueous (36.4% w/w) hydrogen chloride was added into the obtained slurry. The slurry was stirred for 1 hour at room temperature, the solid was then collected by filtration, washed with 6 ml of n-butyl acetate and dried in vacuum. Tomoxetine hydrochloride content: >99% by HPLC assay. Weight: 2.95 g (0.01011 mol). Yield: 79.7%. Atomoxetine hydrochloride enantiomeric ratio: R/S>99/1 (by chiral HPLC)

Example 6

(R)-(−)-N-methyl-3-(2-methylphenoxy)-3-phenyl-propylamine hydrochloride (Atomoxetine Hydrochloride)

7.0 g (0.01718 mol) of (R)-(−)-tomoxetine (S)-(+)-mandelate were mixed at room temperature with 70 ml of ethyl acetate under stirring. Keeping the temperature between 15° C. and 20° C. by means of water-ice bath cooling, gaseous hydrogen chloride was bubbled into the obtained slurry until the congo red indicator paper became blue. The slurry was stirred for 2 hours at room temperature, the solid was then collected by filtration, washed with 3×10 ml of ethyl acetate and dried in vacuum. Tomoxetine hydrochloride content: >99% by HPLC assay. Weight: 4.86 g (0.01665 mol) g. Yield: 97%. Atomoxetine hydrochloride enantiomeric ratio: R/S>99/1 (by chiral HPLC)

Example 7

(R)-(−)-N-methyl-3-(2-methylphenoxy)-3-phenyl-propylamine (Atomoxetine Base Solution)

40 g (0.08697 mol) of (R)-(−)-tomoxetine (S)-(+)-mandelate (88.6% w/w by potentiometric assay) were mixed under stirring with 177.2 ml of n-butyl acetate and 177.2 ml of water. Keeping temperature at 23° C., 17.7 g (about 0.133 mol) of 30% aqueous sodium hydroxide were added. The phases were then separated. The organic phase was washed twice with 35 ml of water each time, then filtered on paper and used as it is for the next step.

Example 8

(R)-(−)-N-methyl-3-(2-methylphenoxy)-3-phenyl-propylamine hydrochloride (Atomoxetine Hydrochloride)

Under stirring and maintaining temperature between 22° C. and 25° C. by means of water bath cooling, 10.07 g (0.09945 mol) of aqueous hydrogen chloride (36%) were dropped on 177 g (0.08648 mol) of atomoxetine base solution (n-butyl acetate), prepared as in Example 7. The hydrochloride then crystallized. The obtained suspension was stirred at about 25° C. for one hour. The solid was collected by filtration and washed twice with 30 ml of n-butyl acetate each time. The solid collected was dried for 18 hours at 70° C. under vacuum. Tomoxetine hydrochloride content: >99% by HPLC assay. Weight: 25.18 g (0.08629 mol). Yield: 99.8%. Atomoxetine hydrochloride enantiomeric ratio: R/S>99/1 (by chiral HPLC)

Example 9

Racemization of Unwanted Enantiomer

About 310 ml of the toluenic solvent mixture ("mother liquors") from optical resolution (e.g. Examples 2-4) were washed with about 50 ml of 2% aqueous sodium hydroxide, then concentrated under vacuum. The oily residue weighed 72.6 g and contained 51.29 g (0.20 mol) of tomoxetine (HPLC assay). 550 g (7.03 mol) of DMSO and 36.7 g (0.60 mol) of potassium hydroxide (bulk industrial grade, 92.1% assay) were added to the concentrate and the mixture was heated between 85° C. and 90° C. until optical rotation of the mixture decreased to 0.00 (3 hours). Heating was stopped, 300 ml of water and 300 ml of toluene were added. The mixture was stirred for some minutes, at which point the phases were separated. The aqueous phase was extracted with 50 ml of toluene. The organic phases were collected and washed with 3×80 ml of water, then concentrated under vacuum. Residue weight: 64.23 g. Tomoxetine content: 49.07 g (0.19 mol) (HPLC assay).

The residue was taken up with 392 ml of toluene and 2.9 ml of methanol, then 17.15 g (0.115 mol) of (S)-(+)-mandelic acid were added to the obtained solution at 25° C. All solids were solubilized by heating to 65°-70° C. The solution was cooled, crude mandelate salt crystallized, was isolated by filtration at 5°-10° C., washed with about 2×40 ml of toluene and dried in vacuum. Weight: 33.6 g. Tomoxetine content: 62.9% by weight (HPLC assay). Yield: 41.2%. Crude mandelate salt (R)-(−)-Tomoxetine enantiomeric ratio: R/S is about 95/5 (by chiral HPLC).

Example 10

Preparation of Atomoxetine Hydrochloride Form A

Thirteen grams (0.03183 mol) of atomoxetine (S)-(+)-mandelate (99.8% w/w by potentiometric assay) was mixed under stirring with 65 ml of isobutyl acetate and 65 ml of water. Keeping the temperature at 20° C., 5.4 g (about 0.0405 mol) of 30% aqueous sodium hydroxide was added and then the phases separated. The organic phase was washed twice with 10 ml of water each time, then filtered on paper, and used for the next step.

Under stirring, and maintaining temperature between 18° C. and 20° C. by means of water bath cooling, 3.27 g (0.03263 mol) of aqueous hydrogen chloride (36.4%) was dropped on 58.2 g (0.02967 mol) of the atomoxetine base solution obtained above. Atomoxetine hydrochloride then crystallized out. The obtained suspension was stirred at about 20° C. for one hour, the solid is collected by filtration, and washed twice with 6 ml of n-butyl acetate. The solid was collected and dried for 18 hours at 45° C. under vacuum.

Example 11

Preparation of Atomoxetine Hydrochloride Forms A & B

Two grams (0.00491 mol) of atomoxetine (S)-(+)-mandelate was mixed at room temperature with 10 ml of toluene and 1 ml of MeOH and under stirring were heated at 60° C. Keeping the temperature at 60° C. by means of oil bath heating, 0.58 g of aqueous (37%) hydrogen chloride was dropped into the obtained solution. The solution was cooled and at 20-25° C. a solid crystallized. The slurry was stirred for 1 hour at 0° C., then the solid was collected by filtration, washed with toluene and dried under vacuum at 45° C. for 5 hours.

Example 12

Preparation of Atomoxetine Hydrochloride Form A

Seven grams (0.01718 mol) of atomoxetine (S)-(+)-mandelate was mixed at room temperature with 70 ml of ethyl acetate under stirring. Keeping the temperature between about 15° C. and about 20° C. by means of water-ice bath cooling, gaseous hydrogen chloride was bubbled into the obtained slurry until Congo red paper became blue. The slurry was stirred for 2 hours at room temperature. The solid was collected by filtration, washed with 3×10 ml of ethyl acetate and dried in vacuo.

Example 13

Preparation of Atomoxetine Hydrochloride Form A

Seven grams (0.01718 mol) of atomoxetine (S)-(+)-mandelate was mixed at room temperature with 70 ml of ethyl acetate under stirring. Keeping the temperature between about 15° C. and about 20° C. by means of water-ice bath cooling, 1.94 g of aqueous (36.3% w/w) hydrogen chloride was added into the obtained slurry. The slurry was stirred for 2 hours at room temperature, then the solid was collected by filtration, washed with 3×10 ml of ethyl acetate and dried in vacuo.

Example 14

Preparation of Atomoxetine Hydrochloride Form A

Atomoxetine (S)-(+)-Mandelate (5.17 g, 0.01267 mol) was mixed at room temperature with 25.5 ml of n-butyl acetate and 0.6 ml of toluene under stirring. Keeping the temperature between about 18° C. and about 20° C. by means of water-ice bath cooling, 1.4 g of aqueous (36.4% w/w) hydrogen chloride was added into the obtained slurry. The slurry was stirred for 1 hour at room temperature. The solid was collected by filtration, washed with 6 ml of n-butyl acetate and dried in vacuo at 65° C.

Example 15

Preparation of Atomoxetine Hydrochloride Form A

Atomoxetine (S)-(+)-mandelate (5.17 g, 0.01267 mol) was mixed at about 50° C. with 25.5 ml of n-butyl acetate and 0.6 ml of toluene under stirring. Keeping the temperature at 50° C. by means of oil bath heating, 1.4 g of aqueous (36.4% w/w) hydrogen chloride was added into the obtained slurry. The slurry that formed was cooled at room temperature and stirred for 1 hour. The solid was collected by filtration, washed with 6 ml of n-butyl acetate and dried in vacuo at 45° C.

We claim:

1. A process for the preparation of crystalline atomoxetine hydrochloride Form A comprising:
    a) combining (R)-(−)-tomoxetine (S)-(+)-mandelate with an organic solvent to obtain a reaction mixture;
    b) combining the reaction mixture of step a) with HCl; and
    c) maintaining the reaction mixture of step (b) to form atomoxetine hydrochloride Form A.

2. A process for the preparation of crystalline atomoxetine hydrochloride Form A comprising:
    a) combining (R)-(−)-tomoxetine (S)-(+)-mandelate with an organic solvent in the presence of water and a base to obtain atomoxetine free base;
    b) combining the atomoxetine free base of step a) with HCl; and
    c) maintaining the reaction mixture of step (b) to form atomoxetine hydrochloride Form A.

3. The process of any one of claims 1 and 2, wherein the organic solvent is selected from the group consisting of aliphatic and aromatic hydrocarbons, $C_{1-4}$ alkyl esters, ketones, linear or branched $C_{4-8}$ alcohols, and mixtures thereof.

4. The process of claim 3 wherein the organic solvent is selected from the group consisting of $C_{5-8}$ alkanes, toluene, xylene, methyl acetate, ethyl acetate, n-butyl acetate, iso-butyl acetate, methyl-ethyl ketone, n-butanol, 2-butanol, n-pentanol, and mixtures thereof.

5. The process of claim 4 wherein the organic solvent is selected from the group consisting of ethyl acetate, n-butyl acetate, and iso-butyl acetate.

6. The process of any one of claims 1 and 2 wherein step b) is carried out at a temperature of about 15° C. to about 50° C.

7. The process of any one of claims 1 and 2 wherein the HCl combined in step b) is either a gas or an aqueous solution.

8. The process of claim 2 wherein, prior to step b), the organic phase is separated from the aqueous phase and HCl is combined with the separated organic phase.

9. The process of claim 2 wherein the amount of water added is about 3 to about 7 ml per gram of (R)-(−)-tomoxetine (S)-(+)-mandelate.

10. The process of claim 9 where the amount of water added is about 5 ml per gram of (R)-(−)-tomoxetine (S)-(+)-mandelate.

11. The process of claim 2 where the base is selected from the group consisting of potassium hydroxide, sodium hydroxide, $Na_2CO_3$, and $K_2CO_3$.

12. The process of claim 11 where the base is sodium hydroxide.

13. A process for the preparation of crystalline atomoxetine hydrochloride Form A comprising:
 a) combining N-methyl-3-hydroxy-3-phenylpropylamine with dimethylsulfoxide (DMSO) in the presence of an alkali metal hydroxide to form a slurry;
 b) adding 2-fluorotoluene to the slurry to obtain a mixture;
 c) heating the resultant mixture to obtain tomoxetine;
 d) combining the obtained tomoxetine with a $C_{1-4}$ alcohol, an aromatic solvent, and (S)-(+)-mandelic acid,
 e) heating the mixture to a temperature of about 60° C. to about 80° C.;
 f) crystallizing (R)-(−)-tomoxetine (S)-(+)-mandelate from the reaction mixture;
 g) adding an organic solvent, and optionally, water and a base to the salt of step f);
 h) combining the mixture of step g) with HCl to form atomoxetine hydrochloride; and
 i) recovering the atomoxetine hydrochloride.

14. The process of claim 13 wherein the DMSO is present at about 0.1 to about 20 moles per mole of N-methyl-3-hydroxy-3-phenylpropylamine.

15. The process of claim 13 wherein the alkali metal hydroxide is combined in step a) in an amount of about 3 to about 5 molar equivalents per molar equivalent of the N-methyl-3-hydroxy-3-phenylpropylamine.

16. The process of claim 13 wherein the mixture in step c) is heated to a temperature from about 80° C. to about 145° C.

17. The process of claim 15 wherein 3 molar equivalents of said alkali metal hydroxide are used, and the mixture in step c) is heated to a temperature of about 135° C. to about 145° C.

18. The process of claim 15 wherein 5 molar equivalents of said alkali metal hydroxide are used, and the mixture in step c) is heated to a temperature of about 80° C. to about 100° C.

19. The process of claim 13 wherein the organic solvent in step g) is added without the base and the water.

20. The process of claim 13 wherein the reaction mixture of step g) is a biphasic system where the HCl is added to the organic phase.

21. The process of claim 13, wherein prior to step g), the obtained (R)-(−)-tomoxetine (S)-(+)-mandelate is recrystallized from a solution comprising an aromatic solvent and a $C_{1-4}$ alcohol.

22. The process of claim 21, wherein the aromatic solvent is toluene, and the $C_{1-4}$ alcohol is methanol.

23. A process for preparing a pharmaceutical composition comprising R(−)-tomoxetine (atomoxetine) or a pharmaceutically acceptable salt thereof, which comprises bringing R(−)-tomoxetine (atomoxetine) or a pharmaceutically acceptable salt thereof prepared according to any one of claims 1, 2, and 13 into contact with one or more pharmaceutically acceptable carriers or excipients.

* * * * *